United States Patent
Dahlhaus

(10) Patent No.: US 6,271,423 B1
(45) Date of Patent: Aug. 7, 2001

(54) PREPARATION OF BUTENYL ETHERS

(75) Inventor: Jürgen Dahlhaus, Limburgerhof (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/445,410

(22) PCT Filed: Jun. 5, 1998

(86) PCT No.: PCT/EP98/03368

§ 371 Date: Dec. 8, 1999

§ 102(e) Date: Dec. 8, 1999

(87) PCT Pub. No.: WO98/57915

PCT Pub. Date: Dec. 23, 1998

(30) Foreign Application Priority Data

Jun. 18, 1997 (DE) .............................................. 197 25 872

(51) Int. Cl.[7] .......................... C07C 41/01; C07C 41/09
(52) U.S. Cl. ..................... 568/689; 568/627; 568/632; 568/633; 568/650; 568/651; 568/654; 568/657; 568/673; 568/675; 568/690; 502/152; 502/155
(58) Field of Search ................................. 568/689, 690, 568/627, 632, 633, 650, 651, 654, 657, 673, 675; 502/152, 155

(56) References Cited

U.S. PATENT DOCUMENTS 5,705,707  1/1998  Kanand et al. ................... 568/487
5,847,166 * 12/1998  Buchwald et al. ................ 549/355

FOREIGN PATENT DOCUMENTS

95/19334  7/1995  (WO) .

OTHER PUBLICATIONS

Snnth, React. Inorg. Met–Org. Chem 15, 109 (1985), Butler et al.
J. Org. Chem., 27 (1971), Bishop et al., 241–249.

* cited by examiner

Primary Examiner—Rosalynd Keys
(74) Attorney, Agent, or Firm—Keil & Weinkauf

(57) ABSTRACT

A process for preparing butenyl ethers of the formula I $$CH_3-CH=CH-CH_2-OR \qquad I$$

by reacting butadiene or butadiene-containing hydrocarbon streams with alcohols of the formula II $$ROH \qquad II$$

at elevated temperature and superatmospheric pressure in the presence of transition metal complexes containing ligands of compounds of elements of group V of the Periodic Table of the Elements to form an isomer mixture of butenyl ethers of the formula I and butenyl ethers of the formula III $$CH_2=CH-CH(OR)-CH_3 \qquad III$$

and, optionally, isomerizing the butenyl ethers of the formula III to butenyl ethers of the formula I, where R is as defined in the specification and the catalyst used is a complex of a transition metal of group VIII of the Periodic Table of the Elements with ligands of the formula IV

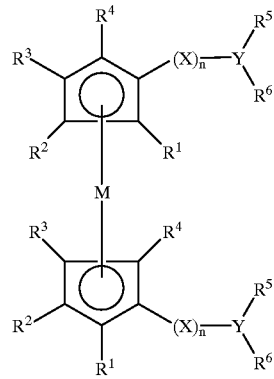

where M is an iron, cobalt, nickel, or ruthenium atom, X is a bridge and where n, y and $R^1$–$R^6$ are as defined in the specification.

10 Claims, No Drawings

PREPARATION OF BUTENYL ETHERS

The present invention relates to a process for preparing butenyl ethers by addition of alcohols onto butadiene in the presence of transition metal complex catalysts containing ligands whose complex-forming centers are joined to a ferrocene cyclopentadienyl radical via atoms of group V of the Periodic Table of the Elements. WO 95/19334 comprehensively describes the preparation of butenyl ethers as intermediates for preparing n-butyraldehyde or n-butanol in the presence of complex catalysts. The process described there opens up a new route for the preparation of n-butyraldehyde and n-butanol compared to the synthesis by means of hydroformylation of propylene generally carried out in industry.

The new process provides a valuable alternative particularly where cheap butadiene is available as starting material.

Although WO 95/19334 has already described a large number of complex catalysts which are suitable for the new preparation of butenyl ethers and enable the industrial synthesis to be carried out in an economically satisfactory yield, certain features are still worthy of improvement.

It is an object of the present invention to provide further improvements, particularly in the combination of the features:

activity and selectivity of the catalyst in respect of the preparation of the desired butenyl ether of the formula I

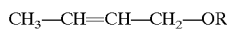
$$CH_3-CH=CH-CH_2-OR \qquad I,$$

little formation of telomeric by-products and easy preparation of the ligand of the complex catalyst.

We have found that this object is achieved by a process for preparing butenyl ethers of the formula I

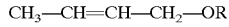
$$CH_3-CH=CH-CH_2-OR \qquad I$$

by reacting butadiene or butadiene-containing hydrocarbon streams with alcohols of the formula II

$$ROH \qquad II$$

at elevated temperature and superatmospheric pressure in the presence of homogeneously dissolved transition metal complexes containing ligands of compounds of elements of group V of the Periodic Table of the Elements to form an isomer mixture of butenyl ethers of the formula I and butenyl ethers of the formula III

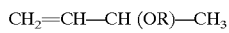
$$CH_2=CH-CH(OR)-CH_3 \qquad III$$

and, if desired, isomerizing the butenyl ethers of the formula III to butenyl ethers of the formula I, where in each case R is an alkyl or alkenyl group having from 1 to 20 carbon atoms, an aryl group having from 6 to 10 carbon atoms or an aralkyl group having from 7 to 11 carbon atoms and the radicals R may be sub-stituted by hydroxy or alkoxy groups, wherein the catalyst used is a complex of a transition metal of group VIII of the Periodic Table of the Elements with ligands of the formula IV

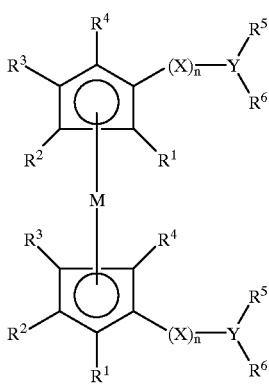

where M is an iron, cobalt, nickel or ruthenium atom, X is a bridge in the form of a substituted or unsubstituted methylene group or an alkyl-substituted silylene group, where n is from 0 to 3, $R^1$ to $R^4$ are, independently of one another, also independently of one another in the two cyclopentadienyl radicals, hydrogen or alkyl, cycloalkyl, aryl or aralkyl radicals having up to 40 carbon atoms, preferably hydrogen or alkyl radicals having from 1 to 4 carbon atoms, or can be part of an isocyclic or heterocyclic ring system, where the two cyclopentadienyl radicals can also be bridged to one another via the respective radicals $R^1$ to $R^4$, Y is nitrogen, arsenic, antimony or phosphorus and the radicals $R^5$ and $R^6$ are, independently of one another, also independently of one another in the two molecules of the sandwich complex, hydrogen or alkyl, cycloalkyl, aryl or aralkyl radicals having up to 24, preferably from 1 to 10, carbon atoms.

Particularly suitable transition metals of group VIII of the Periodic Table of the Elements are nickel and especially palladium.

The complexes can either be produced in situ in the reaction mixture or be preformed and added to the reaction mixture. To produce these complexes in situ, the procedure is generally to introduce the compounds of the transition metals, eg. their halides, preferably their chlorides, bromides or iodides, the nitrates, cyanides or sulfates or preferably complexes of these metals, eg. acetylacetonates, carboxylates, carbonyl complexes or olefin complexes such as ethene or butadiene compleses, together with the ligands into the reaction mixture, whereupon the complexes form in the reaction mixture.

In this procedure, palladium is generally used in the form of palladium dichloride, (dibenzonitrile)palladium dichloride, (diacetonitrile)palladium dichloride and preferably as palladium diacetate and palladium di(acetylacetonate).

Otherwise, the formation of the catalyst occurs in a manner known per se, with the ratio of ligand to palladium being selected in the range from 0.5 to 50, preferably from 1 to 20 and particularly preferably from 2 to 10.

The amount of palladium or the palladium-containing compound is generally from 0.001 to 5% by mass, preferably from 0.01 to 1% by mass, particularly preferably from 0.05 to 0.5% by mass, based on 1,3-butadiene used.

In particular, the ligands of the formula IV to be used according to the present invention contain iron as central atom of the sandwich complex. The substituents $R^1$ and $R^4$ are preferably hydrogen, the value of n is preferably 0 and Y is preferably phosphorus. The radicals $R^5$ and $R^6$ are, in particular, low molecular weight alkyl radicals, cyclohexyl radicals and phenyl radicals. Accordingly, the following individual ligands are found to be useful: 1,11'-bis(diphenylphosphino)ferrocene, 1,1'-bis(diisopropylphosphino) ferrocane1,1'-bis(diethylphosphino) ferrocene, 1,1'-bis(dipropylphosphino)ferrocene, 1'-(diisopropylphosphino)-1'-(dipropylphosphino)ferrocene, 1-(diisopropylphosphino)-1'-(dicyclohexylphosphino) ferrocene and 1,1'-bis(dicyclohexylphosphino)ferrocene.

The preparation of the ligands of the formula IV is either known from the literature or is carried out by methods similar to those described by J. J. Bishop et al. in J. Organometal Chem. 27 (1971) 241–249 and Ian R. Butler et al. in Synth. React. Inorg. Met.-Org. Chem. 15 (1985), (1), 109–116.

The alcohols ROH can in principle be any alcohols depending on which butenyl ethers are to be prepared. However, if the object is to prepare n-butyraldehyde or n-butanol, low molecular weight alcohols and in particular n-butanol are advantageously used.

The addition catalyzed by the complexes to be used according to the present invention and the isomerization are carried out under the same conditions as are described in WO 95/9334. In the addition of the alcohol ROH onto 1,3-butadiene, the molar ratio of 1,3-butadiene/palladium is generally set at from 100:1 to 100,000:1, preferably from 200:1 to 2000:1 and particularly preferably from 400:1 to 1000:1. If the process is carried out continuously, this molar ratio is based on the steady-state 1,3-butadiene concentration in the liquid raction mixture.

In this process embodiment, the molar ratio of alcohol ROH/1,3-butadiene can be selected within wide limits and is generally not critical. For example, the alcohol to be added onto 1,3-butadiene can function not only as a reagent but also as a solvent for the complex catalyst. For this reason, the alcohol/1,3-butadiene molar ratio employed is generally from 1:1 to 10:1, preferably from 1:1 to 5:1 and particularly preferably from 1:1 to 3:1, where these figures are based on the steady-state 1,3-butadiene concentration in the liquid reaction mixture if the process is carried out continuously.

The addition of the alcohol ROH onto 1,3-butadiene is generally carried out in the liquid phase. In general, the catalyst is initially charged as a solution in the liquid reaction medium and 1,3-butadiene in liquid or gaseous form is introduced together with the alcohol into the reaction mixture. The reaction medium employed can be the alcohol to be added onto 1,3-butadiene or a solvent which is inert under the reaction conditions, preferably a high-boiling solvent. Suitable solvents are, for example, condensation products which can be formed during the course of the reaction, for example alkoxyoctadienes, alkoxydodecatrienes, also ethers such as dibutyl ether, dioctyl ether, diethylene glycol dibutyl ether, low molecular weight polyethylene glycol ethers as well as sulfones such as sulfolane, also hydrocarbons such as hexane, decane, benzene, toluene or $C_{10}$–$C_{20}$-hydrocarbon mixtures.

In the batchwise embodiment of the process, the reaction is generally carried out in a stirring autoclave. The adducts of the formulae I and III formed in the reaction are then advantageously removed from the reaction mixture by distillation, with the homocatalyst comprising the palladium or nickel being retained in the distillation bottoms, dissolved in the high-boiling solvent. The catalyst thus remaining in the distillation bottoms can be reused for further reactions.

In the continuous embodiment of the process, the 1,3-butadiene, preferably in liquid form under pressure, is fed into the reaction mixture comprising the alcohol ROH and the homogeneously dissolved transition metal complex catalyst and also, if desired, a high-boiling solvent. The reaction is advantageously carried out in a tube reactor or preferably in a reactor cascade. Unreacted 1,3-butadiene is advantageously circulated. The alcohol ROH is advantageously metered continuously into the reaction mixture at a rate corresponding to that at which it is consumed in the reaction.

According to a further continuous embodiment of the process of the present invention, the 1,3-butadiene can be passed in gaseous form through the catalyst-containing liquid reaction medium, using unreacted 1,3-butadiene for stripping the relatively volatile adducts of the formulae I and II, which have been formed in the reaction with the alcohol, from the reaction mixture. The alcohol ROH can here be continuously metered into the reaction mixture at a rate corresponding to that at which it is consumed in the reaction.

The addition of the alcohol ROH onto 1,3-butadiene in the presence of the complexes to be used according to the present invention is generally carried out at from 20 to 180° C., preferably from 50 to 150° C. and particularly preferably from 50 to 120° C., and at a pressure of from 1 to 50 bar, preferably from 2 to 10 bar and particularly preferably at the pressure established under the reaction conditions.

In place of pure 1,3-butadiene, it is also possible and preferred to use 1,3-butadiene-containing hydrocarbon streams as raw material. Such hydrocarbon streams are formed, for example, as $C_4$ fractions in steam carckers. Before use, these hydrocarbon streams are advantageously freed of any acetylenic or allenic hydrocarbons which may be present therein by partial hydrogenation (Weissermel, Arpe: Industrielle Organische Chemie; 3rd edition, VCH Verlagsgesellschaft, Weinheim 1988). The 1,3-butadiene-containing hydrocarbon streams can then be used as starting material in a similar manner to pure 1,3-butadiene. The saturated or monoolefinic hydrocarbons which are present in these hydrocarbon streams and have not reacted in the reaction are advantageously removed from the reaction product, for example by means of a gas-liquid separator. The adducts of the formulae I and III obtained in the reaction of these hydrocarbon streams can be further processed in the same way as the adducts I and III produced using pure 1,3-butadiene.

The adduct required in the preparation of n-butyraldehyde and/or n-butanol is the 1-alkoxybut-2-ene of the formula I which can be separated from the isomeric 3-alkoxybut-1-ene of the formula III present in the reaction product. Since the adducts I and III are formed in comparable amounts in the addition of the alcohol ROH onto 1,3-butadiene, the process of the present invention would not be economical in industry if it were not possible to convert the 3-alkoxybut-1-ene III into the desired 1-alkoxybut-2-ene I in an economical manner.

For this purpose, the adduct III is first separated from the isomeric adduct I present in the reaction product. This can advantageously be carried out by introducing the reaction product, after prior removal of unreacted 1,3-butadiene, eg. in a gas-liquid separator, into a distillation apparatus and there separating it by fractional distillation.

In this fractional distillation, the by-products which may be present in the reaction product, viz. 1,3-butadiene dimers and trimers and also their adducts with the alcohol ROH and possibly multiply alkoxylated by-products, can also be separated from the adduct I.

The distillative separation of the more volatile adduct III from the adduct I can be carried out in a simple manner, eg. in conventional distillation columns. The adduct III which has been separated from the desired adduct can then, like the unreacted 1,3-butadiene, be returned to the reaction. The recirculation of the adduct III effects the isomerization of the adduct III to the adduct I and finally leads to suppression of new formation of the undesired adduct III, so that when this cyclic procedure is employed, virtually only the desired adduct I but not its undesired isomer III is formed in the overall balance of this cyclic process.

Instead of being recirculated, the adduct III can also be isomerized in a separate isomerization step by passing the adduct III separated from the adduct I through, for example, a reactor charged with a complex catalyst, separating the output of this reactor, which comprises the isomerization mixture of adduct III and adduct I formed therein, into adduct I and adduct III, for example by distillation, if desired further processing the newly formed adduct I and returning the adduct III to the isomerization reactor.

The isomerization of the adduct III to the adduct I in the isomerization reactor can be carried out in the presence or absence of a solvent. This reaction is preferably carried out without solvent. If the isomerization is carried out in the presence of a solvent, use is generally made of high-boiling solvents such as ethers, for example diethylene or triethylene glycol dimethyl ether, diethylene or triethylene glycol dibutyl ether, sulfoxides such as dimethyl sulfoxide or sulfones such as sulfolane, high-boiling aromatic or aliphatic hydrocarbons or halogenated aliphatic or aromatic solvents, eg. dichlorobenzene. The use of low-boiling solvents is likewise possible but generally complicates the distillative separation of the output from the isomerization reactor into the adducts I and III.

The novel process for preparing butenyl ethers is illustrated by the following example.

EXAMPLE

A 150 ml glass pressure vessel was charged with 0.068 g (0.223 mmol) of palladium acetylacetonate, 0.372 g (0.889 mmol) of 1,1'-bis(diisopropylphosphino)ferrocene (prepared as described in J. J. Bishop et al., J. Organomet. Chem. 27 (1971), 241–249), 29.53 g (0.398 mol) of butanol and 17.80 g of a $C_{10}$–$C_{13}$-hydrocarbon mixture under a protective gas atmosphere. 7.92 g (0.146 mol) of 1,3-butadiene were subsequently injected and the mixture was heated to 80° C. The pressure was 1.5 bar. After a reaction time of 35 10 hours, the reaction was stopped and the reaction mixture was analyzed by gas chromatography (GC % by weight). At a butadiene conversion of 56%, the selectivity to 1-butoxybut-2-ene was 32.5% and to 3-butoxybut-1-ene was 66.2%.

We claim:

1. A process for preparing butenyl ethers of the formula I

CH$_3$—CH=CH—CH$_2$—OR        I by reacting butadiene or butadiene-containing hydrocarbon streams with alcohols of the formula II

ROH        II at elevated temperature and superatmospheric pressure in the presence of transition metal complexes containing ligands of compounds of elements of group V of the Periodic Table of the Elements to form an isomer mixture of butenyl ethers of the formula I and butenyl ethers of the formula III

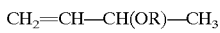

CH$_2$=CH—CH(OR)—CH$_3$        III and, if desired, isomerizing the butenyl ethers of the formula III to butenyl ethers of the formula I, where in each case R is an alkyl or alkenyl group having from 1 to 20 carbon atoms, an aryl group having from 6 to 10 carbon atoms or an aralkyl group having from 7 to 11 carbon atoms and the radicals R may be substituted by hydroxy or alkoxy groups, wherein the catalyst used is a complex of a transition metal of group VIII of the Periodic Table of the Elements with ligands of the formula IV

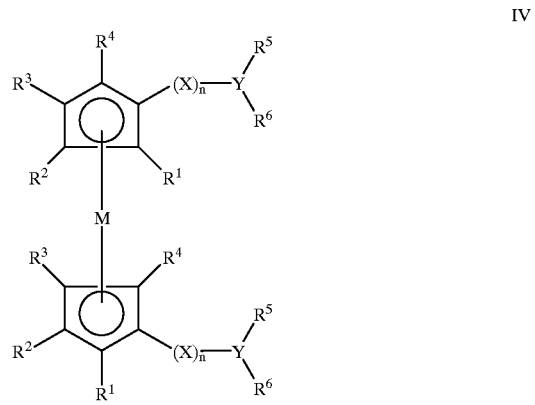

where M is an iron, cobalt, nickel or ruthenium atom, X is a bridge in the form of a substituted or unsubstituted methylene group or an alkyl-substituted silylene group, where n is from 0 to 3, $R^1$ to $R^4$ are, independently of one another, also independently of one another in the two cyclopentadienyl radicals, hydrogen or alkyl, cycloalkyl, aryl or aralkyl radicals having up to 40 carbon atoms or can be part of an isocyclic or heterocyclic ring system, where the two cyclopentadienyl radicals can also be bridged to one another via the respective radicals $R^1$ to $R^4$, Y is nitrogen, arsenic, antimony or phosphorus and the radicals $R^5$ and $R^6$ are, independently of one another, also independently of one another in the two molecules of the sandwich complex, hydrogen or alkyl, cycloalkyl, aryl or aralkyl radicals having up to 24 carbon atoms.

2. A process as defined in claim 1, wherein the transition metal of group VIII of the Periodic Table of the Elements which is used is palladium or nickel.

3. A process as defined in claim 1, wherein the catalyst used is one which can be preformed or obtained in situ by reacting a palladium compound selected from the group consisting of palladium diacetate, palladium di(acetylacetonate), palladium dichloride, (dibenzonitrile) palladium dichloride and (diacetonitrile)palladium dichloride with a ligand of the formula IV.

4. A process as defined in claim 1, wherein the catalyst used contains ligands of the formula IV in which M is an iron atom and Y is phosphorus.

5. A process as defined in claim 1, wherein the catalyst used contains ligands of the formula IV in which the radicals $R^1$ to $R^4$ are hydrogen.

6. A process as defined in claim 1, wherein the catalyst used contains ligands of the formula IV in which n is 0 and $R^5$ and $R^6$ are alkyl, cycloalkyl or aryl radicals having up to 8 carbon atoms.

7. A process as defined in claim 1, wherein the catalyst used contains ligands of the formula IV in which the radicals $R^1$ to $R^4$ are hydrogen, n is 0, Y is phosphorus and $R^5$ and $R^6$ are, independently of one another, low molecular weight alkyl radicals, cyclohexyl radicals or phenyl radicals.

8. A process as defined in claim 1, wherein the catalyst used contains ligands of the formula IV selected from the group consisting of 1,1'-bis(diphenylphosphino)ferrocene, 1,1'-bis(diisopropylphosphino)ferrocene, 1,1'-bisdiethylphosphino)ferrocene, 1,1'-bis(dipropylphosphino)ferrocene, 1-(diisopropylphosphino)-1'-(dipropylphosphino)ferrocene, 1-(diisopropylphosphino)-1'-(dicyclohexylphosphino) ferrocene and 1,1'-bis(dicyclohexylphosphino)ferrocene.

9. A process as defined in claim 1, wherein the isomerization of the enol ether of the formula III to the enol ether of the formula I is carried out in the presence of a catalyst as is used for the addition of the alcohols ROH onto butadiene.

10. A process as defined in claim 1, wherein the alcohols of the formula II which are used are low molecular weight linear aliphatic alcohols.

* * * * *